United States Patent
Ebner (10) Patent No.: US 11,730,887 B2
(45) Date of Patent: Aug. 22, 2023

(54) INJECTION DEVICE WITH A VIBRATION GENERATOR

(71) Applicant: SANOFI, Paris (FR)

(72) Inventor: Catherine Ebner, Frankfurt am Main (DE)

(73) Assignee: Sanofi, Paris (FR)

(*) Notice: Subject to any disclaimer, the term of this patent is extended or adjusted under 35 U.S.C. 154(b) by 166 days.

(21) Appl. No.: 16/756,158

(22) PCT Filed: Oct. 23, 2018

(86) PCT No.: PCT/EP2018/079050
§ 371 (c)(1),
(2) Date: Apr. 15, 2020

(87) PCT Pub. No.: WO2019/081518
PCT Pub. Date: May 2, 2019

(65) Prior Publication Data
US 2020/0276391 A1  Sep. 3, 2020

(30) Foreign Application Priority Data

Oct. 26, 2017 (EP) .................................. 17306471

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31513* (2013.01); *A61M 5/3202* (2013.01);
(Continued)

(58) Field of Classification Search
CPC ........ A61M 5/14248; A61M 2205/581; A61M 2205/582; A61M 2205/50; A61M 2205/52
(Continued)

(56) References Cited

U.S. PATENT DOCUMENTS 5,647,851 A * 7/1997 Pokras ..................... A61M 5/20
                                                             604/131
2003/0040714 A1 * 2/2003 Coss ...................... A61M 5/422
                                                             604/112
(Continued)

FOREIGN PATENT DOCUMENTS

CN   103764206   4/2014
CN   104853788   8/2015
(Continued)

OTHER PUBLICATIONS

PCT International Preliminary Report on Patentability in Application No. PCT/EP2018/079050, dated Apr. 28, 2020, 7 pages.
PCT International Search Report and Written Opinion in Application No. PCT/EP2018/079050, dated Dec. 5, 2018, 16 pages.

*Primary Examiner* — Bhisma Mehta
*Assistant Examiner* — Nidah Hussain
(74) *Attorney, Agent, or Firm* — Fish & Richardson P.C.

(57) ABSTRACT

An injection device is presented. The injection device comprises a housing configured to receive a syringe which has a barrel and a plunger received in the barrel. The injection device further comprises a vibration generator operable to vibrate at least one of the barrel and plunger when said syringe is received in the housing. Methods of dispensing medicament from an injection device are also presented.

22 Claims, 4 Drawing Sheets

(52) U.S. Cl.
CPC .............. *A61M 2205/0294* (2013.01); *A61M 2205/8206* (2013.01)

(58) Field of Classification Search
USPC ........................................................ 604/506
See application file for complete search history.

(56) References Cited

U.S. PATENT DOCUMENTS

| | | | | |
|---|---|---|---|---|
| 2004/0176727 | A1* | 9/2004 | Shekalim | A61M 5/1454 604/181 |
| 2008/0319446 | A1 | 12/2008 | Young | |
| 2010/0041122 | A1* | 2/2010 | Ragsdale | C12M 33/00 435/283.1 |
| 2011/0230837 | A1* | 9/2011 | Kamen | A61M 5/5086 340/687 |
| 2012/0059349 | A1* | 3/2012 | Kuo | A61M 5/14276 141/2 |
| 2015/0122338 | A1* | 5/2015 | Hunter | A61M 5/3146 137/154 |
| 2015/0209522 | A1* | 7/2015 | Jugl | G01H 1/00 73/649 |
| 2015/0253289 | A1 | 9/2015 | Bardina et al. | |

FOREIGN PATENT DOCUMENTS

| | | |
|---|---|---|
| CN | 105188796 | 12/2015 |
| JP | H09-23 9031 | 9/1997 |
| JP | 2006-020843 | 1/2006 |
| JP | 2015-062563 | 4/2015 |
| WO | WO 2008/086560 | 7/2008 |
| WO | WO 2013/034984 | 3/2013 |
| WO | WO 2014/060216 | 4/2014 |
| WO | WO 2014/066937 | 5/2014 |
| WO | WO 2014/100658 | 6/2014 |

\* cited by examiner

INJECTION DEVICE WITH A VIBRATION GENERATOR

CROSS REFERENCE TO RELATED APPLICATIONS

The present application is the national stage entry of International Patent Application No. PCT/EP2018/079050, filed on Oct. 23, 2018, and claims priority to Application No. EP 17306471.8, filed on Oct. 26, 2017, the disclosures of which are incorporated herein by reference.

TECHNICAL FIELD

The present disclosure relates to an injection device and to a method of dispensing medicament from an injection device.

BACKGROUND

Injection devices, such as auto-injectors, are known in the art for dispensing medicament to an injection site of a patient. Such injection devices typically comprise a syringe having a barrel for receiving medicament and a needle at one end of the barrel. The syringe further comprises a plunger that is received in the barrel and a spring for moving the plunger within the barrel to dispense medicament.

To dispense medicament, the needle is first inserted into the body of the patient at the injection site. The plunger is then slid within the barrel by the force of the spring to urge medicament out of the barrel and through the needle to deliver the medicament to the injection site. The plunger must form a tight seal with the barrel to prevent medicament from escaping between the plunger and the barrel.

SUMMARY

It is advantageous to decrease the magnitude of the force that must be exerted on the plunger to move the plunger within the barrel to dispense medicament. This is because decreasing said force reduces the size of the spring that is required to move the plunger and therefore reduces the size and weight of the injection device.

The present disclosure provides an improved injection device and method of dispensing medicament from an injection device.

According to the present disclosure, there is provided an injection device comprising: a housing configured to receive a syringe which has a barrel and a plunger received in the barrel; and, a vibration generator operable to vibrate at least one of the barrel and plunger when said syringe is received in the housing.

Advantageously, the vibration of the barrel and/or plunger can cause the friction and contact time between the barrel and plunger to be reduced. The reduced friction and contact time between the barrel and plunger means that less force is required to move the plunger relative to the barrel to dispense medicament. Therefore, the injection device can be made smaller and lighter and/or the time taken to dispense medicament can be reduced.

The vibration generator may be operable to vibrate the barrel.

Alternatively, or additionally, the vibration generator may be operable to vibrate the plunger. In one embodiment, the vibration generator is configured to be in engagement with the plunger when said syringe is received in the housing such that the vibration generator is operable to vibrate the plunger. In one embodiment, the vibration generator is attached to the plunger to be in engagement with the plunger. In another embodiment, the vibration generator is not attached to the plunger but is in contact with the plunger, for instance, being held against the plunger, to be in engagement with the plunger.

In one embodiment, the plunger is moveable within the barrel to dispense a medicament from the syringe and wherein the vibration generator is configured to move together with the plunger during the dispensing of medicament.

In one embodiment, the plunger comprises a piston and a plunger rod and wherein the vibration generator is operable to vibrate at least one of the piston and the plunger rod.

In one embodiment, the vibration generator comprises a piezoelectric transducer.

In one embodiment, the barrel has an eigenfrequency/natural frequency and wherein the vibration generator is operable to vibrate said at least one of the barrel and plunger at a frequency different to said eigenfrequency and, optionally, at a frequency greater than said eigenfrequency.

In one embodiment, the vibration generator is operable to vibrate said at least one of the barrel and plunger at a frequency in the range of 100 to 3000 Hz. This range of frequencies has been found to advantageously reduce the friction between the plunger and barrel whilst also reducing the user's perception of the vibrations.

The injection device may further comprise an actuator that can be actuated by a user to operate the vibration generator. The actuator may comprise, for example, a switch or button. In one embodiment, the injection device further comprises a medicament dispensing mechanism configured to move the plunger relative to the barrel to dispense medicament contained in the barrel when said syringe is received in the housing, wherein actuation of the actuator operates the medicament dispensing mechanism.

The injection device may further comprise an energy storage configured to power the vibration generator.

In one embodiment, the injection device further comprises a cap configured to cover a needle of said syringe when said syringe is received in the housing. The cap may be removably attachable to the housing.

In one embodiment, the housing entirely contains the barrel of the syringe when the syringe is received in the housing. In one embodiment, the entire axial length of the barrel of the syringe is contained within the housing.

In one embodiment, the vibration generator is received in the housing.

The injection device may further comprise a syringe that is received in the housing, wherein the syringe comprises a barrel and a plunger received in the barrel. In one such embodiment, the barrel contains a medicament.

In one embodiment, the injection device is an auto-injector.

In one embodiment, there is provided an injection device comprising: a housing configured to receive a syringe which has a barrel and a plunger received in the barrel; and, a vibration generator configured to be in engagement with the plunger when said syringe is received in the housing such that the vibration generator is operable to vibrate the plunger.

According to the present disclosure, there is also provided a method of dispensing medicament from an injection device, the injection device comprising a syringe that has a barrel containing medicament and a plunger received in the barrel, the method comprising: vibrating at least one of the barrel and plunger; and, exerting a force on the plunger to slide the plunger within the barrel.

In one embodiment, the method comprises vibrating at least one of the barrel and plunger using a vibration generator. The vibration generator may be in engagement with the plunger to vibrate the plunger.

These and other aspects of the disclosure will be apparent from and elucidated with reference to the embodiments described hereinafter.

BRIEF DESCRIPTION OF THE FIGURES

Examples of embodiments of the disclosure will now be described with reference to the accompanying drawings, in which.

DETAILED DESCRIPTION

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml.

Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least one of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
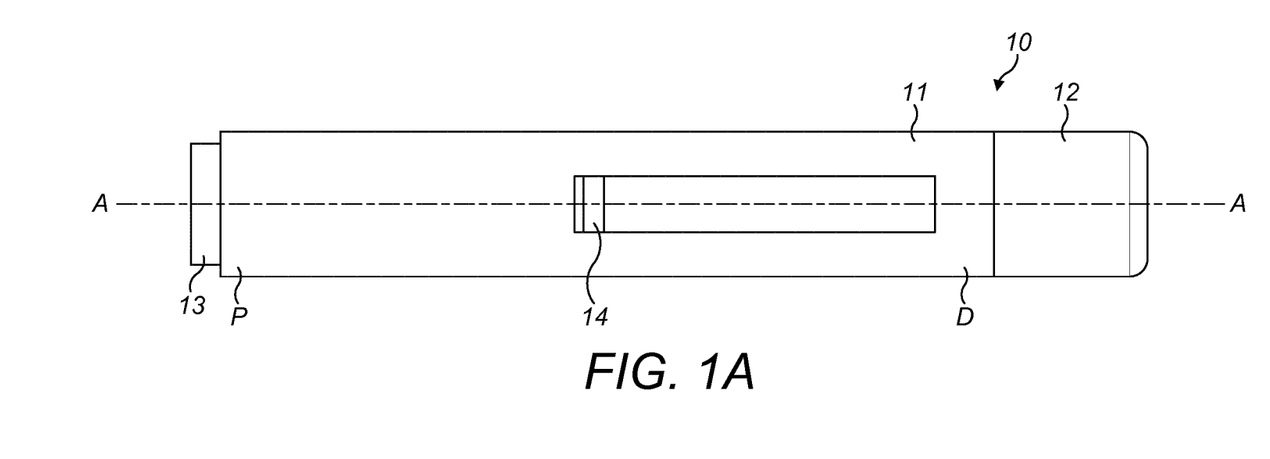
FIG. 1A is a schematic side view of an auto-injector with a cap attached to a housing of the auto-injector according to embodiments of the present disclosure.
Figure 1B:
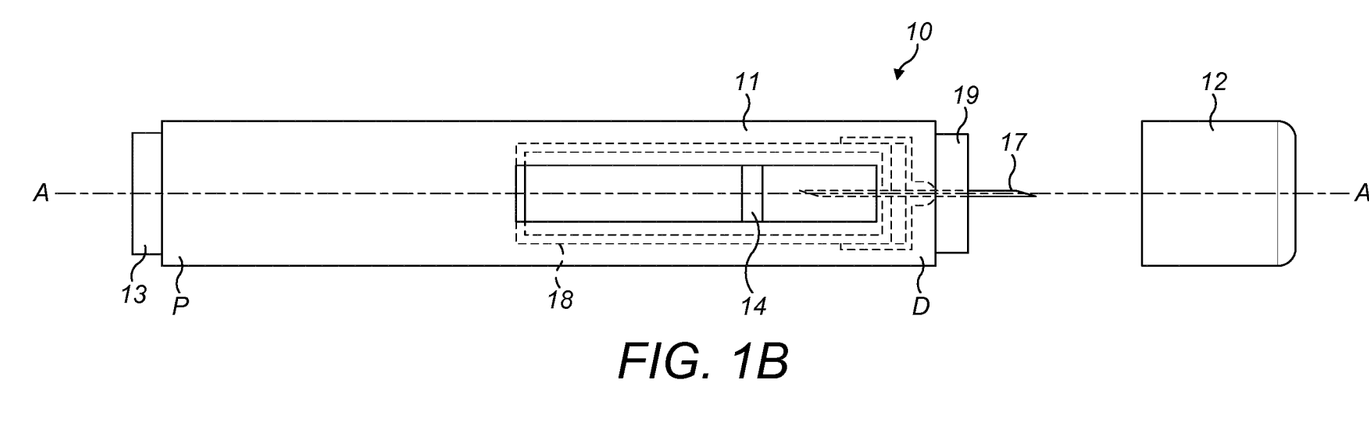
FIG. 1B is a schematic side view of the auto-injector of FIG. 1A, with the cap removed from the housing.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
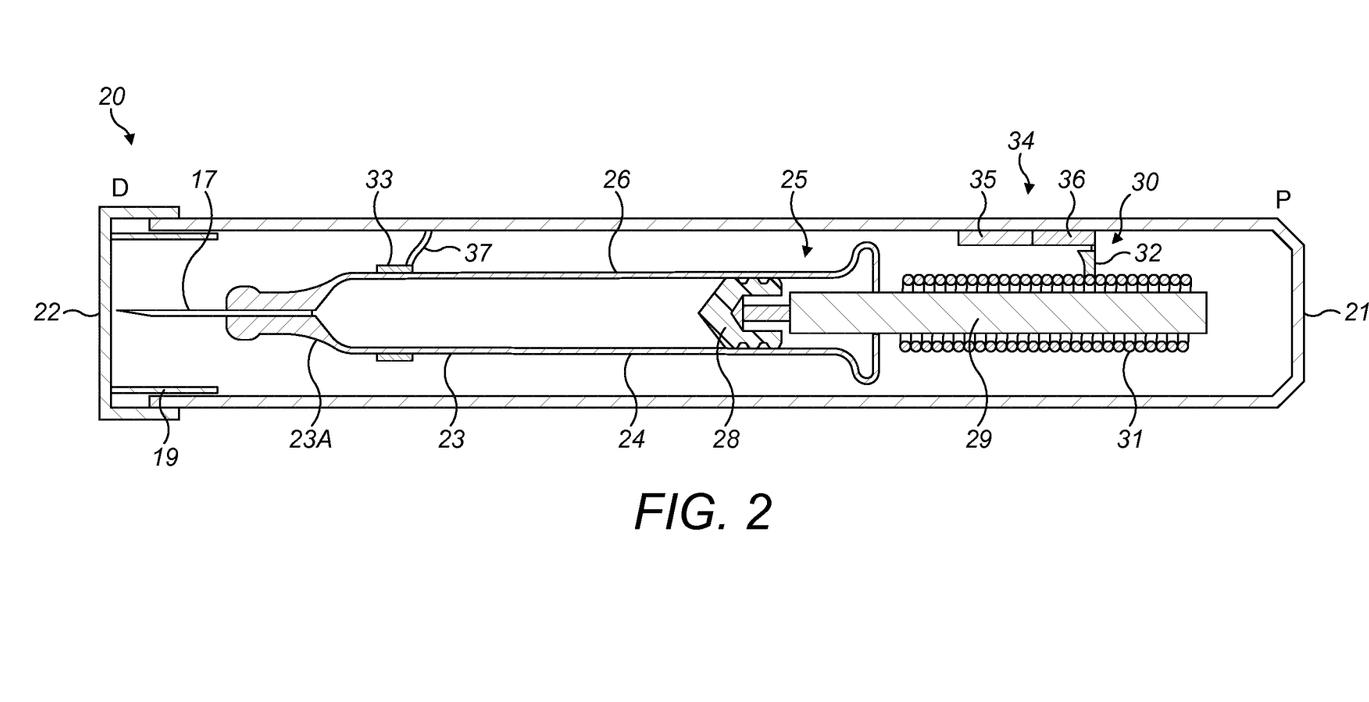
FIG. 2 is a schematic cross-sectional side view of an auto-injector according to a first embodiment of the present disclosure.

Referring to FIG. 2, an injection device 20 according to a first embodiment of the present disclosure is shown. The injection device 20 is in the form of an auto-injector 20 that has some similar features to the auto-injector 10 described above in relation to FIGS. 1A and 1B, with like features retaining the same reference numerals.

The injection device 20 comprises a housing 21 and a cap 22 that is removably attachable to the distal region D of the housing 21.

A syringe 23 is disposed within the housing 21. The syringe 23 comprises a barrel 24 and a plunger 25. The barrel 24 includes a cylindrical peripheral wall 26. A needle 17 is located at a needle end 23A of the syringe 23 for dispensing medicament from the barrel 24.

The plunger 25 comprises a piston 28 and a plunger rod 29 that is connected at one end to the piston 28. The piston 28 is received in the barrel 24 and is slidable from a first position (shown in FIG. 2) to a second position (not shown). When the piston 28 is in the first position, the piston 28 is spaced from the needle end 23A of the syringe 23 such that a chamber is formed therebetween which is filled with medicament. When the piston 28 is moved to the second position, the piston 28 is slid towards the needle end 23A of the syringe 23 to urge the medicament out of the barrel 24 and through the needle 17.

The injection device 20 further comprises a medicament delivery mechanism 30 configured to move the piston 28 from the first position to the second position. The medicament delivery mechanism 30 comprises a biasing member 31 and a latch 32.

The biasing member 31 is in the form of a spring 31. However, it should be recognised that in alternative embodiments a different type of biasing member 31 may be implemented, for example, a portion of resilient material that is compressed or put under tension to bias the piston 28 towards the second position.

A first end of the spring 31 is connected to the housing 21 towards the proximal region P thereof. A second end of the spring 31 is connected to the plunger rod 29. The spring 31 is compressed when the piston 28 is in the first position to exert a force on the plunger rod 29 that urges the piston 28 towards the distal region D of the housing 21. Thus, the piston 28 is biased into the second position by the spring 31.

The latch 32 is configured to initially hold the plunger rod 29 against the force of the spring 31 such that the piston 28 is retained in the first position. The latch 32 is connected to an actuator (not shown), which in the present embodiment comprises a button. The actuator is provided on the housing 21 and can be pressed by the user to release the latch 32 such that the force of the spring 31 slides the piston 28 towards the needle end 23A of the syringe 23 to dispense medicament out of the needle 17.

The injection device 20 further comprises a vibration generator 33 and an energy source 34.

The vibration generator 33 is in the form of a piezoelectric transducer 33. The piezoelectric transducer 33 is attached to the outer surface of the peripheral wall 26 of the barrel 24. In the present embodiment, the piezoelectric transducer 33 is located towards the needle end 23A of the syringe 23. However, it should be recognised that the piezoelectric transducer 33 may alternatively be attached to another portion of the barrel 24, for example, to the needle end 23A of the syringe 23 or to a portion of the peripheral wall 26 of the barrel 24 nearer to the proximal region P of the housing 21. In one embodiment, the piezoelectric transducer 33 is attached to the inner surface of the peripheral wall 26 of the barrel 24.

The energy source 34 is disposed within the housing 21 and is configured to power the vibration generator 33. The energy source 34 comprises a battery 35 and a control circuit 36.

The energy source 34 is configured to supply a signal of varying voltage to the piezoelectric transducer 33 to induce the piezoelectric transducer 33 to repeatedly change shape such that the piezoelectric transducer 33 vibrates, which in turn vibrates the peripheral wall 26 of the barrel 24. In the present embodiment, the battery 35 supplies power to the control circuit 36 which generates a waveform that is output to the piezoelectric generator 33 via a cable 37.

In one embodiment, the control circuit 36 comprises a waveform generator and may be configured to output, for example, a square wave, sinusoidal wave or triangular wave. The battery 35 may output a constant voltage DC signal and the control circuit 36 may be configured to convert this into a varying voltage DC signal that powers the piezoelectric transducer 33. In some embodiments, the control circuit 36 comprises, for example, an oscillator, inverter, or other waveform generator. However, it should be recognised that other forms of power electronics are also capable of supplying the piezoelectric transducer 33 with a signal that induces vibration of the piezoelectric transducer 33. In one alternative embodiment, the battery 35 is omitted and instead the piezoelectric transducer 33 is electrically connected to an external power source, for example, a waveform generator or AC power source, to induce the piezoelectric transducer 33 to vibrate.

To deliver medicament to a patient, the cap 22 is first removed from the housing 21 such that the needle sleeve 19 protrudes from the distal region D of the housing 21 to shield the needle 17. The distal end of the needle sleeve 19 is then pressed against an injection site of the patient such that the needle sleeve 19 retracts into the housing 21 and the needle 17 enters the injection site.

The patient then presses the actuator (not shown). This causes the energy source 34 to supply power to the piezoelectric transducer 33 such that the piezoelectric transducer 33 starts to vibrate, which vibrates the peripheral wall 26 of the barrel 24. In one embodiment, depression of the actuator closes a switch (not shown) to electrically connect the energy source 34 to the piezoelectric transducer 33. In another embodiment, depression of the actuator operates the control circuit 36 such that a signal of varying voltage is output from the control circuit 36 to induce vibration of the piezoelectric element 33.

When the actuator is pressed by the patient, the latch 32 is also released such that the compressed spring 31 exerts a force on the piston rod 29 to slide the piston 28 within the barrel 24 towards the needle end 23A of the syringe 23. The movement of the piston 28 within the barrel 24, from the first position towards the second position, forces the medicament in the barrel 24 to flow out of the needle 17 and into the injection site of the patient.

The vibration of the barrel 24 induced by the piezoelectric element 33 causes the friction and contact time between the barrel 24 and the piston 28 to be reduced. The reduced friction between the barrel 24 and piston 28 is due to the fact that the dynamic friction between the barrel 24 and piston 28 is less than the static friction therebetween that is present when the barrel 24 is not vibrating.

The reduced friction and contact time between the barrel 24 and piston 28 means that less force is required to slide the piston 28 within the barrel 24 to dispense medicament. Therefore, the spring 31, and thus the injection device 20, can be made smaller and lighter than if the injection device 20 did not include a vibration generator 33 that vibrates the barrel 24.

Alternatively, if the spring 31 is kept the same size then the time taken to dispense the medicament will be of shorter duration because the reduced friction and contact time between the barrel 24 and piston 28 will result in the piston 24 taking less time to travel from the first position to the second position within the barrel 24 for a given force applied to the plunger rod 29.

In the above described embodiment, the piezoelectric transducer 33 is attached to the barrel 24, which does not move relative to the energy source 34 during the dispensing of medicament out of the needle 17. Therefore, it is relatively easy to maintain a stable electrical connection between the piezoelectric transducer 33 and energy source 34 using the cable 37.

Figure 3:
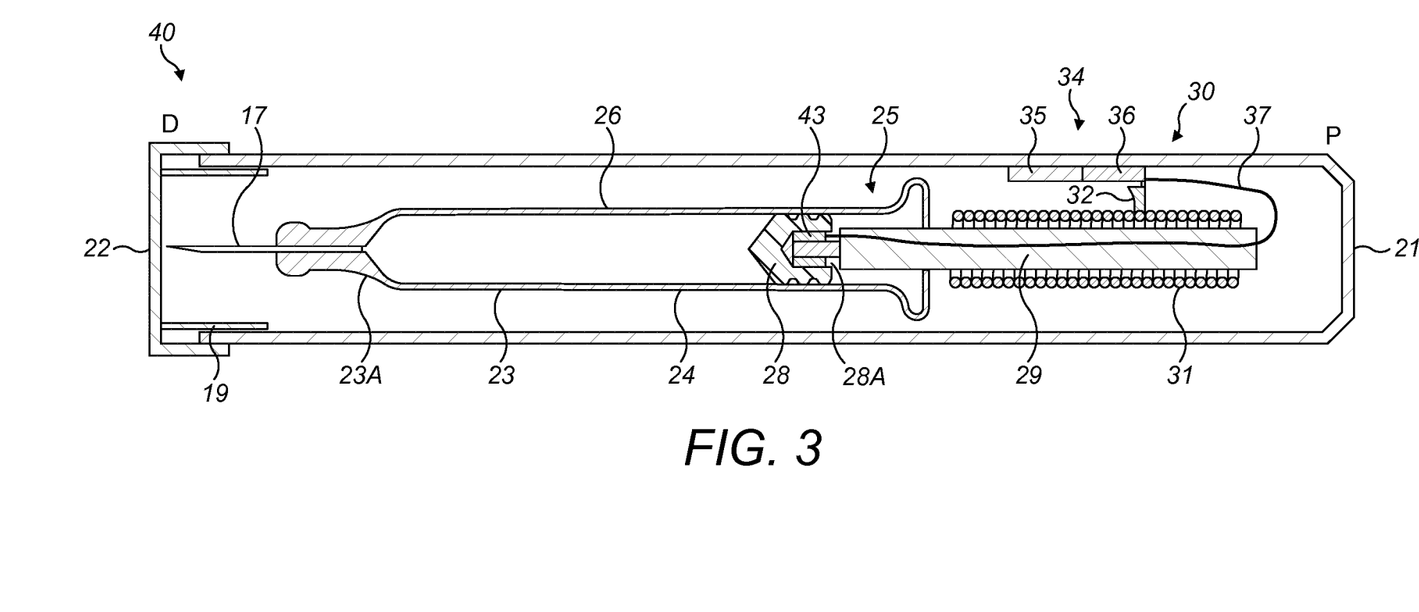
FIG. 3 is a schematic cross-sectional side view of an auto-injector according to a second embodiment of the present disclosure; and, FIG. 4 is a schematic cross-sectional side view of an auto-injector according to a third embodiment of the present disclosure.

Referring now to FIG. 3, an injection device 40 according to a second embodiment of the present disclosure is shown. The injection device 40 is in the form of an auto-injector 40 that has similar features to the auto-injector 20 described above in relation to FIG. 2, with like features retaining the same reference numerals. A difference is that the vibration generator 33 of the auto-injector 20 of the first embodiment is omitted and is replaced with an alternative vibration generator 43.

The vibration generator 43 is in the form of a piezoelectric transducer 43. The piezoelectric transducer 43 is attached to the plunger 25. More specifically, the piezoelectric transducer 43 is attached to the piston 28 of the plunger 25. In the present embodiment, the piston 28 comprises a central recess 28A and the piezoelectric transducer 43 is located in the recess 28A. However, it should be recognised that the piezoelectric transducer 43 may alternatively be attached to another portion of the piston 28, for example, the piezoelectric transducer 43 may be attached to an end of the piston 28 or may be embedded into the material of the piston 28. In one embodiment, the piezoelectric transducer 43 is adhered to the piston 28 or attached thereto by an interference fit. In one embodiment, the plunger rod 29 exerts a force on the piezoelectric transducer 43 to hold the piezoelectric transducer 43 against the piston 28.

Similarly to the injection device 20 of the first embodiment described above in relation to FIG. 2, the energy source 34 is configured to supply a signal of varying voltage to the piezoelectric transducer 43 to induce vibration of the piezoelectric transducer 43. However, due to the positioning of the piezoelectric transducer 43 of the second embodiment, the vibration of the piezoelectric transducer 43 vibrates the piston 28.

To deliver medicament to a patient, the cap 22 is removed from the housing 21 and the distal end of the needle sleeve 19 is pressed against an injection site of the patient such that the needle sleeve 19 retracts into the housing 21 and the needle 17 enters the injection site.

The patient then presses the actuator (not shown). This causes the energy source 34 to power the piezoelectric transducer 43 such that the piezoelectric transducer 43 starts to vibrate, resulting in vibration of the piston 28. Actuation of the actuator by the patient also causes the latch 32 to be released such that the compressed spring 31 exerts a force on the piston rod 29 to slide the piston 28 within the barrel 24 towards the needle end 23A of the syringe 23. Thus, medicament is dispensed to the injection site of the patient via the needle 17.

The vibration of the piston 28 induced by the piezoelectric transducer 43 causes the friction and contact time between the barrel 24 and the piston 28 to be reduced. As described above in relation to the first embodiment, the reduced friction and contact time between the barrel 24 and piston 28 means that less force is required to slide the piston 28 within the barrel 24 to dispense medicament. Therefore, the spring 31, and thus the injection device 40, can be made smaller and lighter than if the injection device 40 did not include a vibration generator 43. Alternatively, the spring 31 can be kept the same size to apply the same magnitude of force to the plunger rod 29, in which case the reduced friction and contact time between the barrel 24 and piston 28 will result in a reduction in the time taken for the piston 28 to move from the first position to the second position and therefore an increase of the medicament delivery flow rate.

In the second embodiment, the piezoelectric transducer 43 is arranged to vibrate the piston 28. This provides the technical advantage that the reduction of the friction and contact time between the barrel 24 and piston 28 remains relatively constant regardless of the position of the piston 28 within the barrel 24. In comparison, the level of reduction of the friction and contact time between the barrel 24 and piston 28 of the injection device 20 of the first embodiment described above is dependent on the position of the piston 28 within the barrel 24. This is because when the piston 28 slides within the barrel 24 away from the first position to dispense medicament, the piston 28 moves closer to the vibrating piezoelectric transducer 33 such that the friction and contact time between the barrel 24 and piston 28 is altered. On the contrary, the injection device 40 of the second embodiment alleviates this problem because the distances between the piezoelectric element 43 and the piston 28 and peripheral wall 26 of the barrel 24 remain constant regardless of the position of the piston 28 within the barrel 24.

Figure 4:
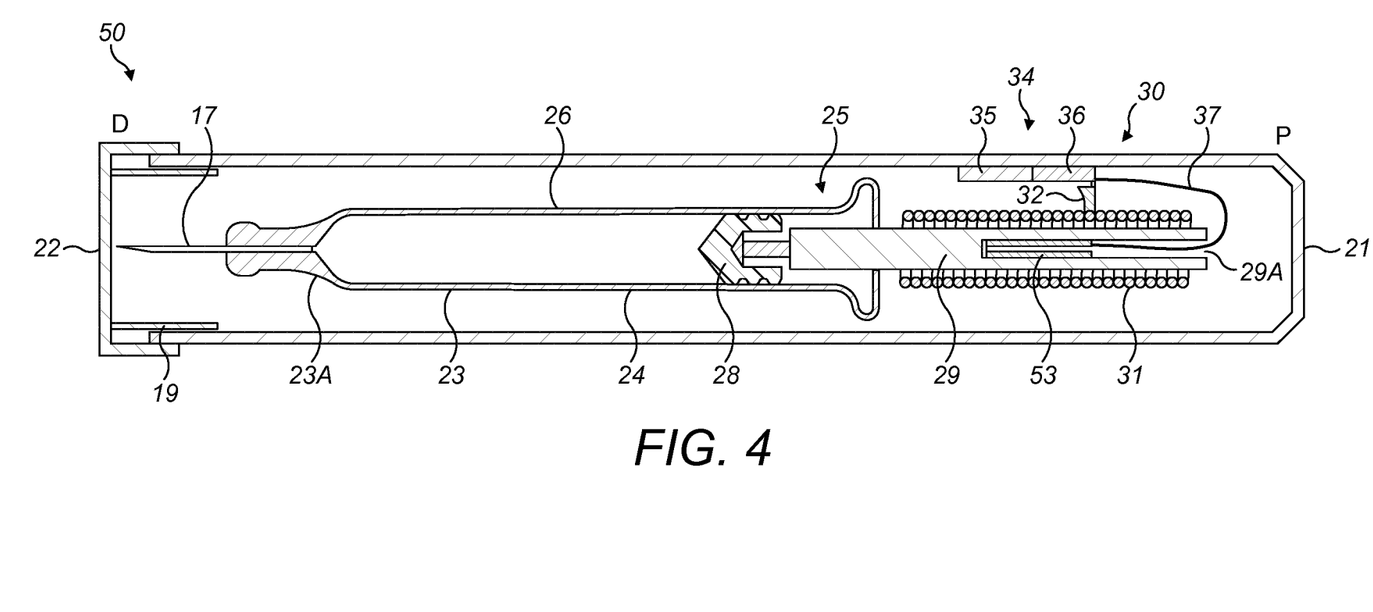

Referring now to FIG. 4, an injection device 50 according to a third embodiment of the present disclosure is shown. The injection device 50 is in the form of an auto-injector 50 that has similar features to the auto-injector 20 described above in relation to FIG. 2, with like features retaining the same reference numerals. A difference is that the vibration generator 33 of the auto-injector 20 of the first embodiment is omitted and is replaced with an alternative vibration generator 53.

The vibration generator 53 is in the form of a piezoelectric transducer 53. The piezoelectric transducer 53 is attached to the plunger 25. More specifically, the piezoelectric transducer 53 is attached to the plunger rod 29 of the plunger 25. In the present embodiment, the plunger rod 29 comprises a central recess 29A and the piezoelectric transducer 53 is located in the recess 29A. However, it should be recognised that the piezoelectric transducer 53 may alternatively be attached to another part of the plunger rod 29. For example, the piezoelectric transducer 53 may be attached to the proximal or distal end of the plunger rod 29 or may be embedded into the material of the plunger rod 29. In one embodiment, the piezoelectric transducer 53 is adhered to the plunger rod 29 or attached thereto by an interference fit. In one embodiment, the piezoelectric transducer 53 is provided on the outside of the peripheral surface of the plunger rod 29.

Similarly to the injection device 20 of the first embodiment described above in relation to FIG. 2, the energy source 34 is configured to supply a signal of varying voltage to the piezoelectric transducer 53 to induce vibration of the piezoelectric transducer 53. However, due to the position of the piezoelectric transducer 53 of the third embodiment, the vibration of the piezoelectric transducer 53 vibrates the plunger rod 29. The piston 28 is attached to the distal end of the plunger rod 29 and therefore vibration of the plunger rod 29 causes vibration of the piston 28. The plunger rod 29 may be manufactured from a stiff material, for example, plastic, glass, or metal, to promote the transfer of vibrations through the plunger rod 29 to the piston 28.

To deliver medicament to a patient, the cap 22 is removed from the housing 21 and the distal end of the needle sleeve 19 is then pressed against an injection site of the patient such that the needle sleeve 19 retracts into the housing 21 and the needle 17 enters the injection site.

The patient then presses the actuator (not shown). This causes the energy source 34 to power the piezoelectric transducer 53 such that the piezoelectric transducer 53 starts to vibrate, resulting in vibration of the plunger rod 29 and thus the piston 28. Depression of the actuator by the patient also causes the latch 32 to be released such that the compressed spring 31 exerts a force on the piston rod 29 to slide the piston 28 within the barrel 24 towards the needle end 23A of the syringe 23. Thus, medicament is dispensed to the injection site of the patient via the needle 17.

The vibration of the plunger rod 29, and thus the piston 28, causes the friction and contact time between the barrel 24 and the piston 28 to be reduced. As described above in relation to the first and second embodiments, the reduced friction and contact time between the barrel 24 and piston 28 results in less force being required to slide the piston 28 within the barrel 24 to dispense medicament. Therefore, the spring 31, and thus the injection device 50, can be made smaller and lighter than if the injection device 50 did not include a vibration generator 53. Alternatively, the spring 31 can be kept the same size to apply the same magnitude of force to the plunger rod 29, in which case the reduced friction and contact time between the barrel 24 and piston 28 increases the medicament delivery flow rate.

In the second embodiment, the piezoelectric transducer 53 is arranged to vibrate the plunger rod 29, which in turn vibrates the piston 28. This provides the technical advantage that the reduction of the friction and contact time between the barrel 24 and piston 28 remains relatively constant regardless of the position of the piston 28 within the barrel 24. In comparison, the level of reduction of the friction and contact time between the barrel 24 and piston 28 of the injection device 20 of the first embodiment described above is dependent on the position of the piston 28 within the barrel 24. As discussed above, this is because when the piston 28 of the first embodiment slides within the barrel 24 to move away from the first position to dispense medicament, the piston 28 moves closer to the piezoelectric transducer 33 such that the friction and contact time between the barrel 24 and piston 28 is altered. On the contrary, the injection device 50 of the third embodiment alleviates this problem because the distance between the piston 28 and the piezoelectric transducer 53 remains constant regardless of the position of the piston 28 within the barrel 24.

In addition, the piezoelectric transducer 53 being arranged to vibrate the plunger rod 29 provides the advantage that the injection device 50 can easily be used with existing syringes 23 without requiring modification of the barrel 24 or piston 28. For example, the housing 21 may comprise an opening to allow for insertion of a syringe 23 comprising a needle 17, a barrel 24 containing medicament and a piston 28. The plunger rod 29, with the piezoelectric transducer 53 attached thereto, is then brought into contact with the piston 28 such that the injection device 50 is ready for delivering medicament upon removal of the cap 22 from the housing 21.

The vibrations induced by the vibration generator 33, 43, 53 may be carried through the needle 17 and/or housing 21 such that the vibrations are felt by the patient. To prevent or alleviate this, in the above described embodiments the vibration generator 33, 43, 53 is configured to vibrate at a frequency of greater than 100 Hz. It has been found that when the frequency of vibration is greater than 100 Hz, the vibrations are not as readily perceived by the patient. In one embodiment, the vibration generator 33, 43, 53 is configured to vibrate at a frequency of less than 3000 Hz. In one embodiment, the vibration generator 33, 43, 53 is configured to vibrate at a frequency in the range of 100 to 3000 Hz. However, it should be recognised that in alternative embodiments (not shown) the vibration generator is configured to vibrate at a different frequency.

In some embodiments, the vibration generator 33, 43, 53 is configured to vibrate at a frequency different to the eigenfrequency of the barrel 24. This helps to prevent damage to the barrel 24 when the vibration generator 33, 43, 53 is operated. In one such embodiment, the vibration generator 33, 43, 53 is configured to vibrate at a frequency greater than the eigenfrequency of the barrel 24.

The eigenfrequency of the barrel 24 may, for example, be in the range of 20 to 150 Hz. For instance, in one embodiment the barrel 24 has a capacity of 1 ml and an eigenfrequency of 70 Hz. The eigenfrequency of the barrel 24 will depend on the capacity of the barrel 24 and also the material used to manufacture the barrel 24. Typically, barrels having larger capacities have lower eigenfrequencies.

In the above described embodiments, the vibration generator 33, 43, 53 is in the form of a piezoelectric element 33, 43, 53. However, it should be recognised that other types of vibration generator 33, 43, 53 are also intended to fall within the scope of the present disclosure. In one embodiment (not shown), the vibration generator comprises an electric motor having a rotor with a weight eccentrically mounted to the rotor. The rotor is rotated to move the weight about an eccentric path of rotation which generates vibrations. The frequency of vibration is dependent on the speed of rotation of the rotor.

In another embodiment (not shown), the vibration generator comprises a linear actuator that is driven in a reciprocal motion to induce vibrations. The linear actuator may be driven in a reciprocal motion against a part of the injection device, for example, the barrel or plunger, to cause said part of the injection device to vibrate. In one embodiment, the linear actuator comprises an electric motor which drives a pinion gear that engages with a rack gear. The electric motor rotates the pinion gear alternately in first and second rotational directions to drive the rack gear in a reciprocal motion to generate vibrations. In another embodiment (not shown), the linear actuator comprises a linear solenoid. The linear solenoid is driven in a reciprocal motion to generate vibrations.

In some embodiments (not shown), the energy source instead comprises a dynamo that may be turned by a crank to power the vibration generator. Alternatively, the vibration generator may be connected to mains power.

In the above described embodiments, the piezoelectric transducer 33, 43, 53 is electrically connected to the energy source 34 via a cable 37. However, in alternative embodiments (not shown) the piezoelectric transducer is instead electrically connected to the energy source via a printed circuit board (PCB) or by making one or more of the components of the injection device conductive. For example, if the piezoelectric transducer is attached to the piston then the cable may be connected to the plunger rod which is manufactured from a conductive material to electrically connect the cable to the piston.

In the first, second and third embodiments of the injection device 20, 40, 50 described above, the vibration generator 33, 43, 53 is only attached to one of the barrel 24, piston 28 and plunger rod 29. However, in alternative embodiments (not shown), the injection device may comprise a plurality of vibration generators that are attached to the barrel and/or the plunger. For example, a first vibration generator may be attached to the barrel and a second vibration generator may be attached to the piston.

In the above described embodiments, the vibration generator 33, 43, 53 is attached directly to the barrel 24 or to the piston 28 or plunger rod 29 of the plunger 25. However, it should be recognised that in alternative embodiments (not shown), the vibration generator may be attached to another part of the injection device which transfers the vibrations to induce the barrel or plunger to vibrate.

In some embodiments, the barrel 24 of the injection device 20, 40, 50 contains a medicament having a high viscosity. It has been found that medicament having a high viscosity may increase the drug delivery time and/or increase the force that must be exerted on the piston 28 in order to force the medicament out of the needle 17. The vibration generator 33, 43, 53 reduces the injection time and/or force that must be exerted on the piston to dispense medicament. Therefore, at least some of the embodiments of the present disclosure help to alleviate the increased drug delivery time and/or increased delivery force associated with delivering high viscosity medicament. In some embodiments, the medicament has a viscosity greater than 6 cP. The medicament may have a viscosity greater than 10 cP, 20 cP, 30 cP, 40 cP or 50 cP. However, it should be recognized that embodiments of the present disclosure can also be suitable for use with medicaments having a viscosity different to those discussed above.

In the above described embodiments, the injection device 20, 40, 50 comprises an actuator (not shown) in the form of a button that is pressed to operate the vibration generator and also commence the delivery of medicament. In an alternative embodiment, the actuator comprises an alternative configuration, for example, being in the form of a switch or lever. In one embodiment (not shown), the needle sleeve comprises the actuator. Therefore, when the needle sleeve is pressed against the injection site of the patient the vibration generator is operated and/or medicament is dispensed through the needle for delivery to the injection site. In one embodiment, the vibration generator is operated upon removal of the cap from the housing of the injection device. For instance, the injection device may comprise a switch that is closed when the cap is removed from the housing to operate the vibration generator. In one embodiment (not shown), the injection device comprises a first actuator that may be actuated to operate the vibration generator and a second actuator that may be actuated to dispense medicament.

In the above described embodiments, the needle 17 is fixedly located relative to housing 21 and initially located within the needle sleeve 19. Proximal movement of the needle sleeve 19 by placing a distal end of sleeve 19 against a patient's body and moving housing 21 in a distal direction will uncover the distal end of needle 17. As discussed above in relations to FIGS. 1A and 1B, such relative movement allows the distal end of needle 17 to extend into the patient's body and such insertion is termed "manual" insertion because the needle 17 is manually inserted via the patient's manual movement of housing 21 relative to needle sleeve 19. However, in alternative embodiments (not shown), the insertion is "automated" such that the needle moves relative to housing to enter the injection site. Such insertion can be triggered by movement of the needle sleeve or by another form of activation, for example, being controlled by the actuator that controls the vibration generator and drug delivery or by a further actuator.

In the above described embodiments, the injection device 20, 40, 50 is in the form of an auto-injector 20, 40, 50. However, it should be recognised that in alternative embodiments the injection device may comprise a different form of drug delivery system, for example, a large volume device (LVD).

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-Cb10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injection device comprising:
   a housing configured to receive a syringe that has a barrel and a plunger received in the barrel;
   a medicament dispensing mechanism configured to move the plunger relative to the barrel to dispense medicament contained in the barrel when the syringe is received in the housing; and
   a vibration generator operable to vibrate the plunger whilst the plunger is moving relative to the barrel to dispense the medicament when the syringe is received in the housing, wherein the vibration generator is configured to move together with the plunger during dispensing of the medicament.

2. The injection device according to claim 1, wherein the plunger comprises a piston and a plunger rod, and wherein the vibration generator is operable to vibrate at least one of the piston or the plunger rod.

3. The injection device according to claim 1, wherein the vibration generator is configured to be in engagement with the plunger when the syringe is received in the housing such that the vibration generator is operable to vibrate the plunger.

4. The injection device according to claim 1, wherein the plunger is moveable within the barrel to dispense the medicament from the syringe.

5. The injection device according to claim 1, wherein the vibration generator comprises a piezoelectric transducer.

6. The injection device according to claim 1, wherein the barrel has an eigenfrequency, and wherein the vibration generator is operable to vibrate the plunger at a vibration frequency different from the eigenfrequency of the barrel.

7. The injection device according to claim 6, wherein the vibration frequency is greater than the eigenfrequency.

8. The injection device according to claim 1, wherein the vibration generator is operable to vibrate the plunger at a frequency in a range of 100 to 3000 Hz.

9. The injection device according to claim 1, further comprising an actuator configured to be actuated by a user to operate the vibration generator.

10. The injection device of claim 9, wherein an actuation of the actuator operates the medicament dispensing mechanism.

11. The injection device according to claim 1, further comprising an energy storage configured to power the vibration generator.

12. The injection device according to claim 1, further comprising a cap configured to cover a needle of the syringe when the syringe is received in the housing.

13. The injection device according to claim 1, wherein the housing entirely contains the barrel of the syringe when the syringe is received in the housing.

14. The injection device according to claim 1, wherein the vibration generator is disposed in the housing.

15. The injection device according to claim 1, wherein the injection device is an auto-injector.

16. The injection device according to claim 1, wherein the vibration generator is configured to be attached to the plunger when the syringe is received in the housing such that the vibration generator is operable to vibrate the plunger.

17. The injection device according to claim 16, wherein the plunger comprises a central recess and wherein the vibration generator is configured to be received in the central recess.

18. The injection device according to claim 1, wherein the vibration generator is operable to vibrate the plunger whilst the plunger is moving relative to the barrel when the syringe is received in the housing in order to reduce a force required to move the plunger relative to the barrel.

19. The injection device according to claim 1, wherein the medicament dispensing mechanism comprises a biasing member configured to exert a force on the plunger to move the plunger relative to the barrel.

20. The injection device according to claim 19, wherein the biasing member comprises a spring.

21. A method of dispensing a medicament from an injection device, the method comprising:
   exerting a force on a plunger to slide the plunger within a barrel to dispense the medicament; and
   vibrating the plunger of a syringe of the injection device whilst the force is being exerted on the plunger such that a vibration generator moves together with the plunger during dispensing of the medicament.

22. The method of claim 21, wherein vibrating the plunger is performed at a frequency different from an eigenfrequency of the barrel.

\* \* \* \* \*